(12) United States Patent
Chen et al.

(10) Patent No.: US 7,104,406 B2
(45) Date of Patent: Sep. 12, 2006

(54) MICRO-FILTER FOR FILTERING BLOOD CELLS

(75) Inventors: Wae-Honge Chen, Tainan (TW); Kai Cheng Chang, Taipei (TW); Guang-Chyeng Fan, Hsinchu (TW); Pei-Fang Liang, Yun Lin Hsien (TW)

(73) Assignee: Industrial Technology Research Institute, Hsinchu Hsien (TW)

( * ) Notice: Subject to any disclaimer, the term of this patent is extended or adjusted under 35 U.S.C. 154(b) by 386 days.

(21) Appl. No.: 10/642,299

(22) Filed: Aug. 18, 2003

(65) Prior Publication Data

US 2005/0040098 A1 Feb. 24, 2005

(51) Int. Cl.
*B01D 29/07* (2006.01)
*B01D 25/00* (2006.01)
*B01D 61/14* (2006.01)

(52) U.S. Cl. ............... 210/498; 210/348; 210/483; 210/488; 210/645; 210/650; 422/68.1; 422/101; 422/102; 422/129; 422/138; 137/833; 137/827; 137/550; 366/341

(58) Field of Classification Search ............... 210/498, 210/348, 483, 488, 645, 650; 422/68.1, 101, 422/102, 129, 138; 137/833; 366/341
See application file for complete search history.

(56) References Cited

U.S. PATENT DOCUMENTS

| | | | |
|---|---|---|---|
| 5,256,360 A | 10/1993 | Li | |
| 5,690,763 A * | 11/1997 | Ashmead et al. | 156/60 |
| 5,811,062 A * | 9/1998 | Wegeng et al. | 422/129 |
| 6,409,072 B1 * | 6/2002 | Breuer et al. | 228/111.5 |
| 6,814,859 B1 * | 11/2004 | Koehler et al. | 210/198.2 |
| 2004/0053422 A1 * | 3/2004 | Chan et al. | 436/180 |

* cited by examiner

*Primary Examiner*—Krishnan S. Menon
(74) *Attorney, Agent, or Firm*—Rabin & Berdo, P.C.

(57) ABSTRACT

A micro-filter for filtering blood cells has a plurality of filtering channel structures, each having a first through hole and a first concave portion connecting to each other, and a plurality of through channel structures respectively connect to the filtering channel structures. Each defines a second through hole opposite the first concave portion, whereby the filtering channel structures are respectively attached to the through channel structures to provide more than two filtering effects.

5 Claims, 10 Drawing Sheets

MICRO-FILTER FOR FILTERING BLOOD CELLS

BACKGROUND OF THE INVENTION (1) Field of the Invention

The present invention relates to a micro-filter for filtering blood cells, and more particularly to a two-channel structure made by MEMS (Micro-Electro-Mechanical Systems) technology, whereby a different channel width between the two channel structures is used to provide more than two filtering effects.

(2) Description of the Related Art

The trend in articles and instruments for medical purposes already is towards small size and personal scale. In general, a filtering instrument can be used to separate the blood cells into leukocytes, erythrocytes, hematoblasts and serums according to the size of the blood cells, but the filtering instrument is too big and expensive. The prior art is exemplified by the disclosure of U.S. Pat. No. 5,256,360, with reference to FIG. 1. A micro-mold 1a is manufactured using micro-machining technology (such as micro-electrical-discharge machining technology, laser-beam micro-machining and electron beam micro-machining), and a molding material is placed in the micro-mold 1a. The molding material is allowed to solidify to form a micro-filter. Referring to FIGS. 2 and 3, the micro-filter has a plurality of channels 2a for filtering one type of blood cells, so that the micro-filter is not only expensive to manufacture, but also incapable of filtering more that one type of blood cell.

SUMMARY OF THE INVENTION

It is an object of the present invention is to provide a micro-filter for filtering blood cells, wherein two channel structures connect with each other and are made by MEMS technology, whereby the different channel widths of the two channel structures are used to filter blood cells of different sizes.

It is another object of the present invention to provide a micro-filter for filtering blood cells, wherein the micro-filter is made by MEMS technology for reducing the dimensions and the manufacturing cost of the micro-filter.

In accordance with one aspect of the present invention, a micro-filter is provided for filtering blood cells. The micro-filter comprises a plurality of filtering channel structures each having a first through hole and a first concave portion connecting with each other. The first concave portion defines two first channel portion opposite each other, and a plurality of through channel structures respectively connecting to the filtering channel structures and each defining a second through hole connecting with the first concave portion.

It is to be understood that both the foregoing general description and the following detailed description are exemplary, and are intended to provide further explanation of the invention as claimed. Other advantages and features of the invention will be apparent from the following description, drawings and claims.

BRIEF DESCRIPTION OF THE DRAWINGS

Other objects, features and advantages of the present invention will be more apparent from the following detailed description when read in conjunction with the accompanying drawings in which.

DETAILED DESCRIPTION OF THE PREFERRED EMBODIMENT

A description will now be given of the preferred embodiments of the present invention with reference to the accompanying drawings.

Figure 1:
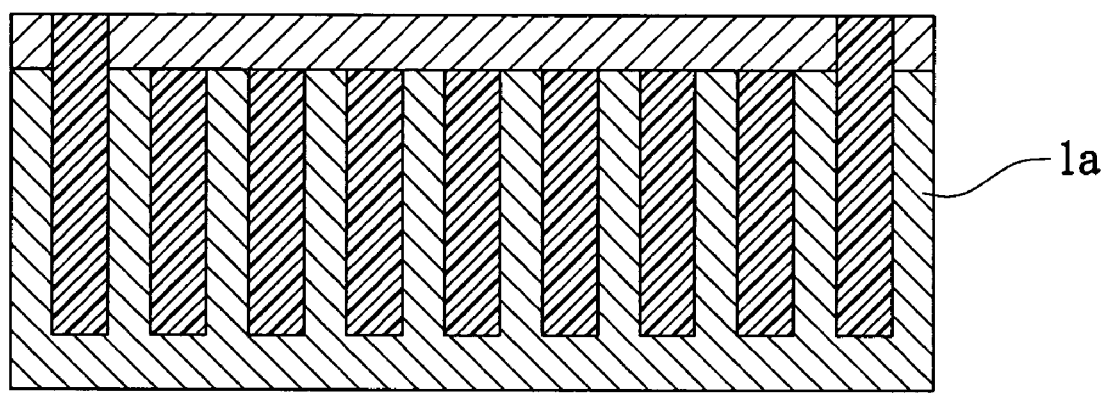
FIG. 1 is a schematic cross-sectional view of the micro-mold of the micro-filter.
Figure 2:
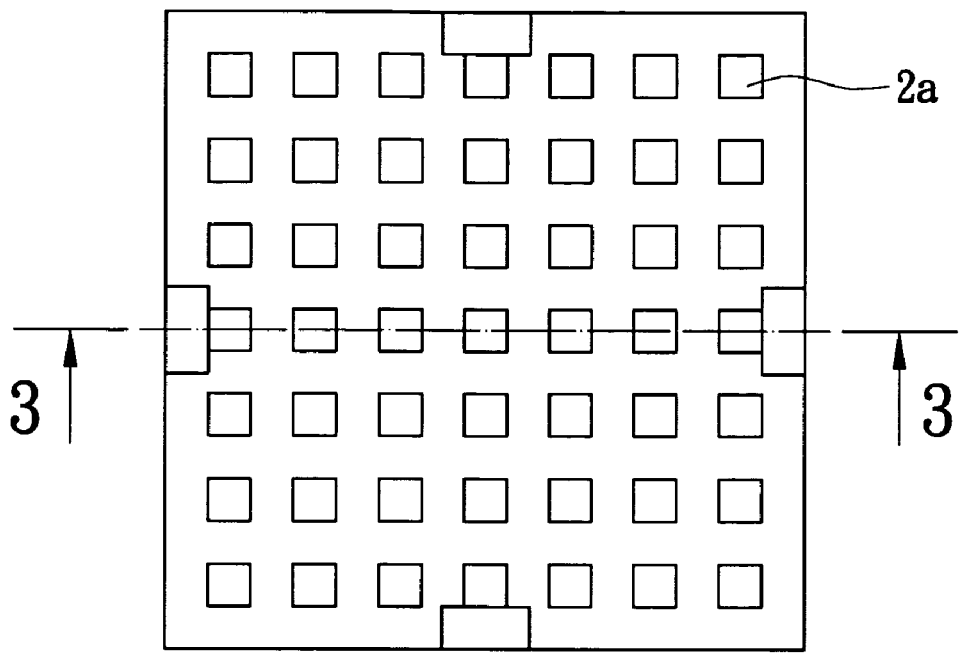
FIG. 2 is a schematic top view of the micro-filter according to the prior art.
Figure 3:
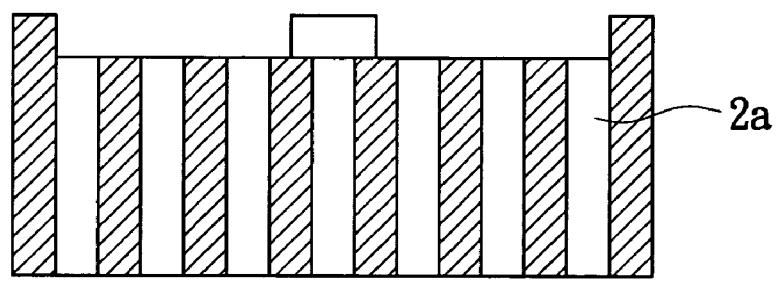
FIG. 3 is a schematic cross-sectional view of the micro-filter along line 3—3 in FIG. 2 according to the prior art.
Figure 4:
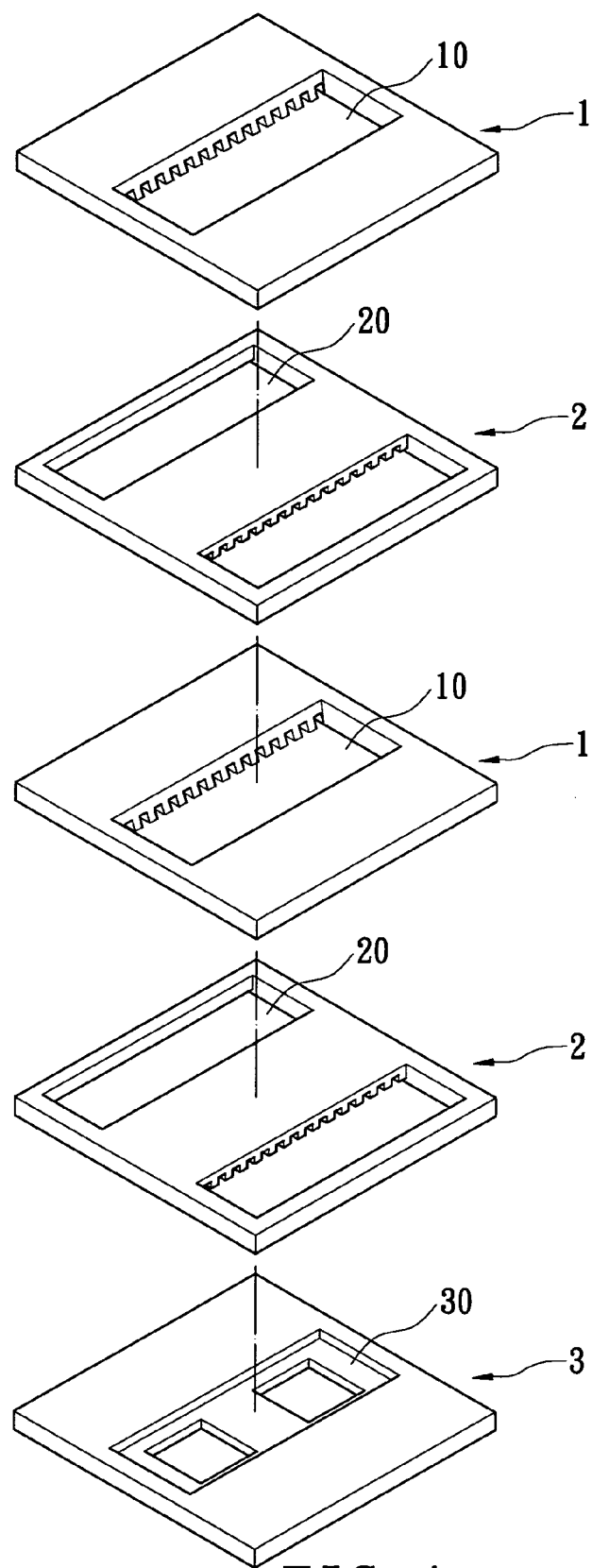
FIG. 4 is a schematic perspective view of the micro-filter according to the present invention.
Figure 5:
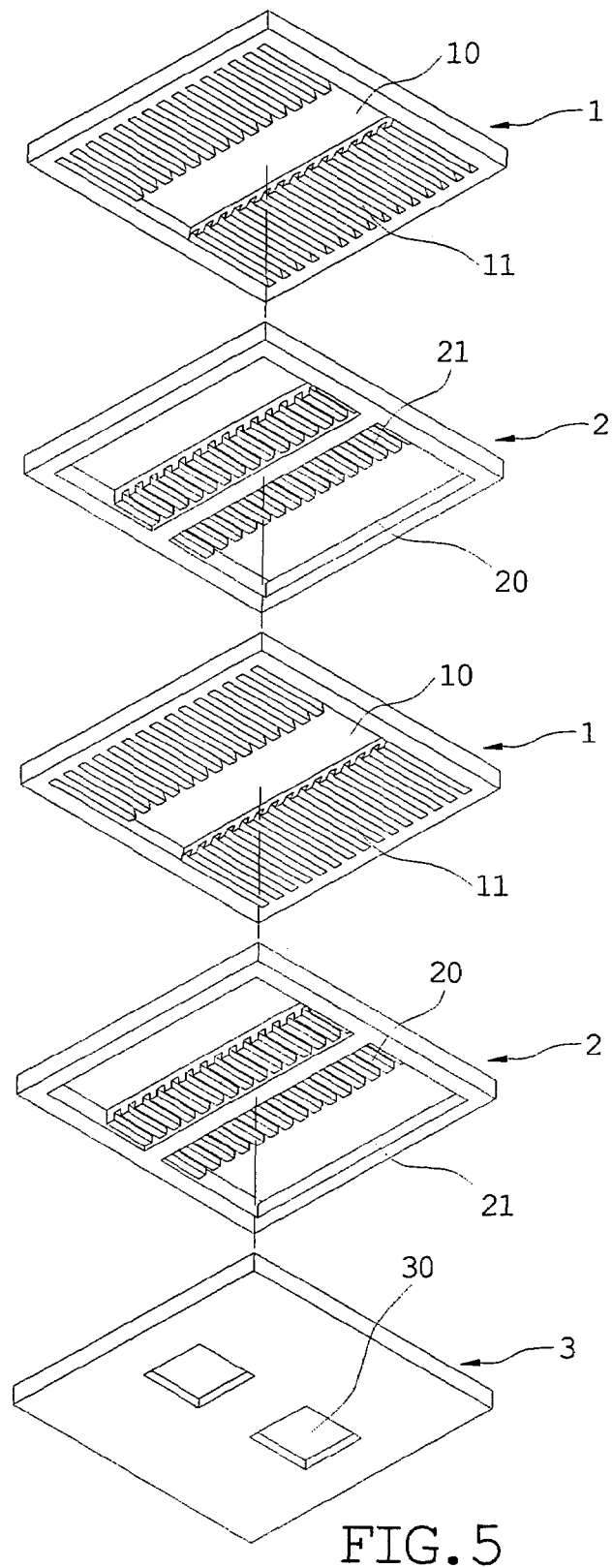
FIG. 5 is a schematic perspective view of the micro-filter according to the present invention.
Figure 6:
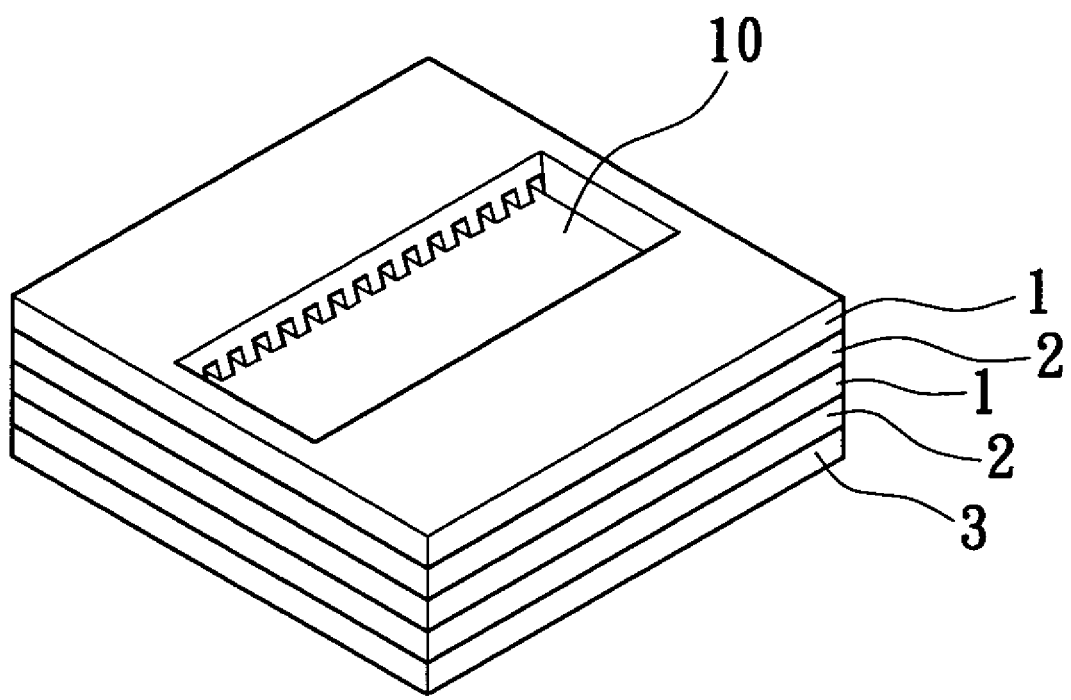
FIG. 6 is a schematic assembly view of the micro-filter.

Referring to FIGS. 4 to 6, the present invention provides a micro-filter for filtering blood cells, which includes a plurality of filtering channel structures 1, through channel structures 2 and a base structure 3.

Figure 7:
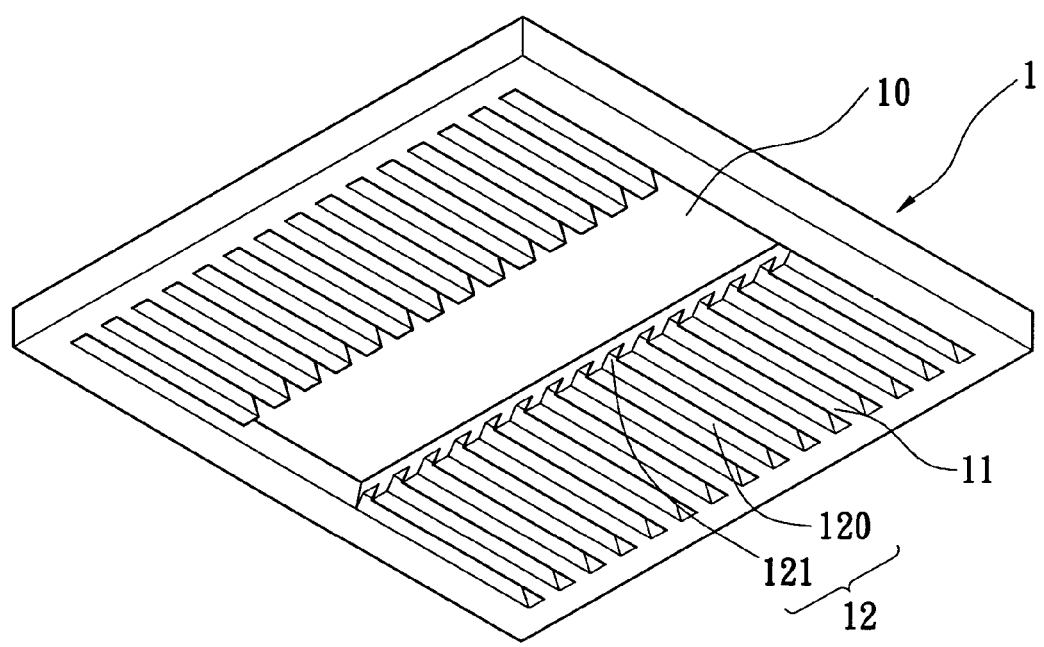
FIG. 7 is a schematic perspective view of the filtering channel structure according to the present invention.
Figure 8:
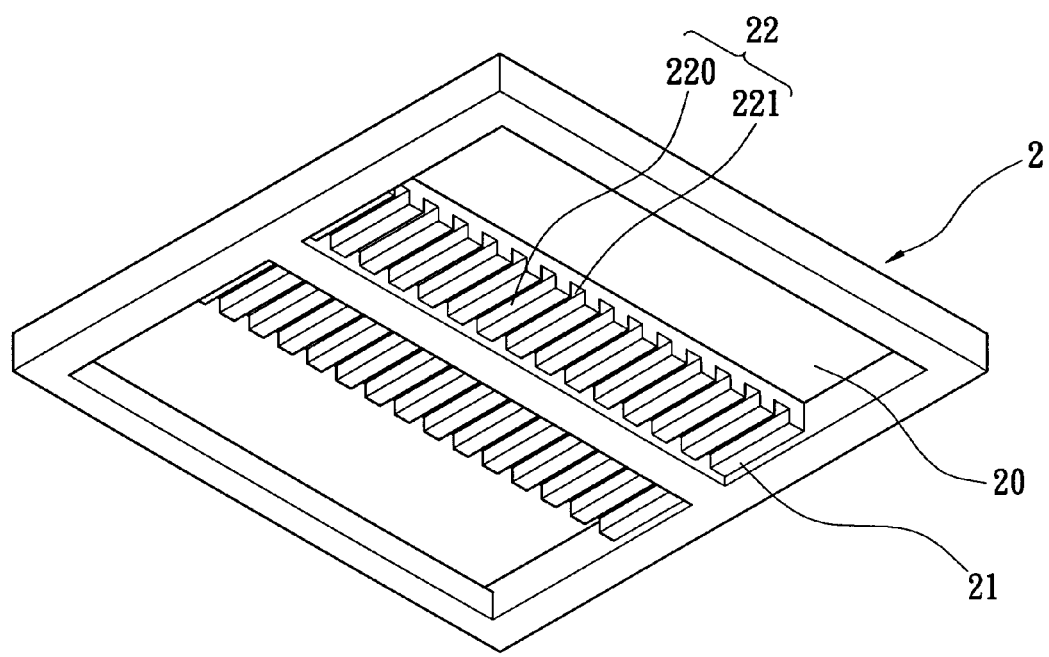
FIG. 8 is a schematic perspective view of the through channel structure according to the present invention.

Referring to FIG. 7, each of the filtering channel structures 1 has a first through hole 10 and a first concave portion 11 connected to each other, the first concave portion 10 defining two first channel portions 12 opposite each other, and each of the first channel portions 12 having a plurality of channels 120 and openings 121. Referring to FIG. 8, each of the through channel structures 2 respectively connects to the filtering channel structures 1 by an anode joint so as to provide more than two filtering effects. The filtering channel structures and the through channel structures are made of a silicon wafer. Each of the through channel structures 2 defines a second through hole 20 and a second concave portion 21 connected to each other. The second through hole 20 is opposite the first concave portion 11, and the second concave portion 21 defines two second channel portions 22 opposite each other. Each of the second channel portions 22 has a plurality of channels 220 and openings 221. A base structure 3 is connected to a bottom of the through channel structures 2 and has a plurality of through hole 30 therein to strengthen the micro-filter.

FIGS. 4 and 5 show the structures 1, 2, and 3 exploded from their assembled combination and retaining their assembled orientations. FIGS. 4 and 5 show that, in the assembly, the channels 120 of channel structure 1 are parallel to the channels 220 of channel structure 2.

Figure 9:
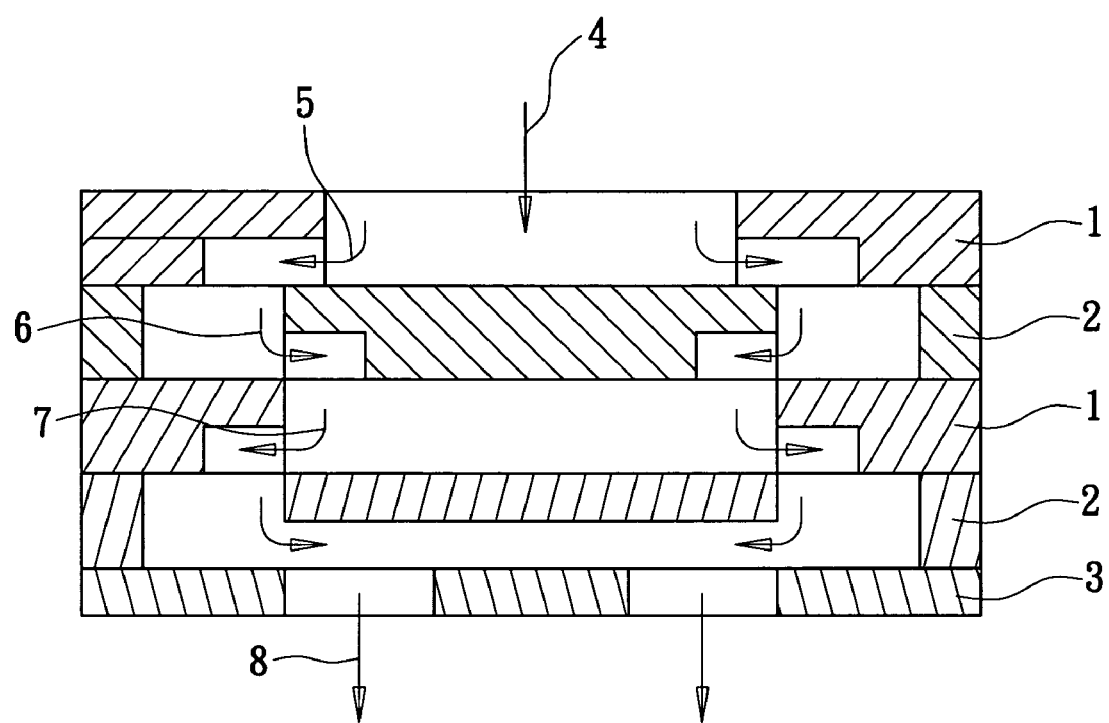
FIG. 9 is a schematic view of the micro-filter used to filter the blood cells according to the present invention.
Figure 10:
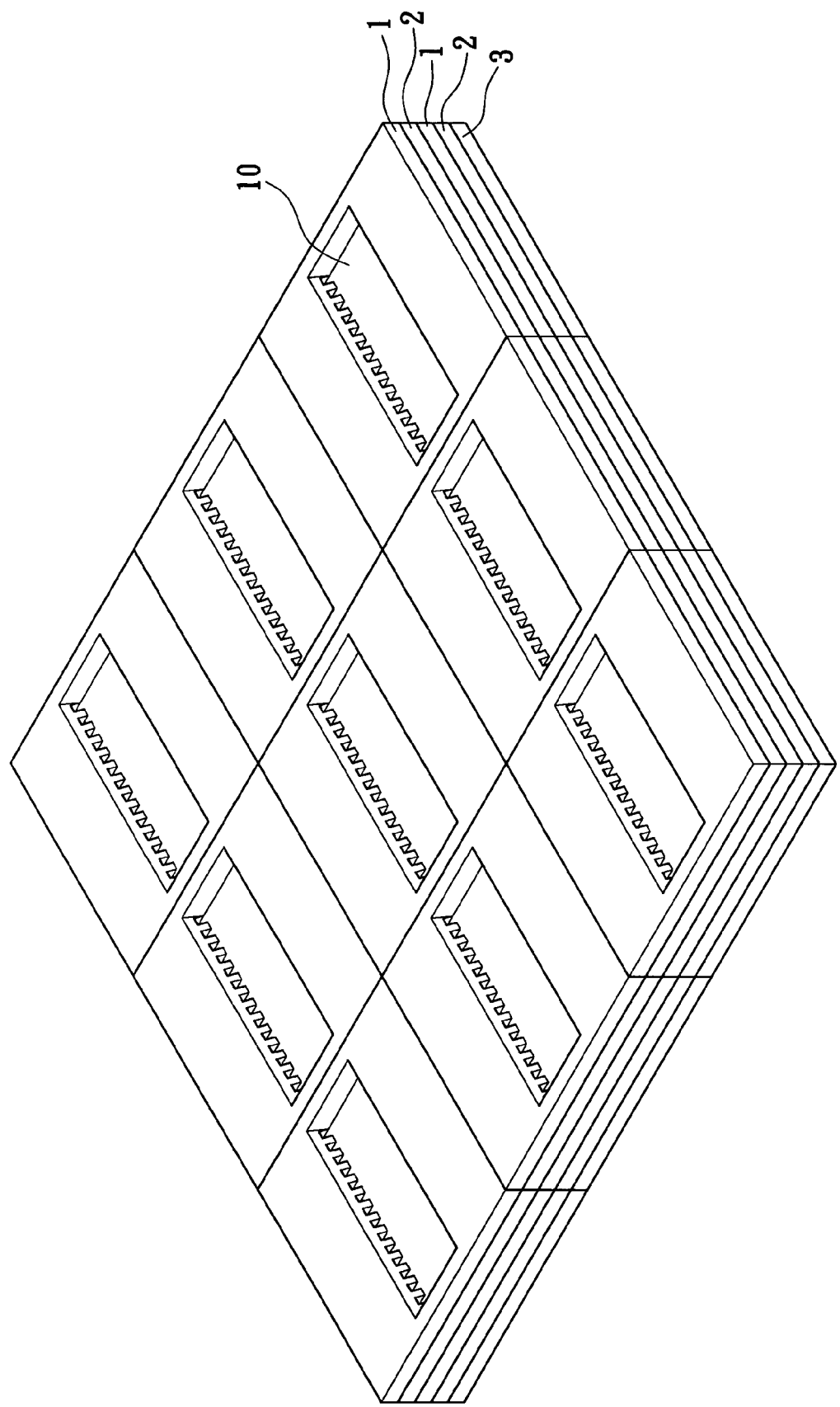
FIG. 10 is a schematic assembly view of the micro-filter arranged in the array according to the present invention.

Referring to FIG. 9, the filtering channel structures 1 are respectively connected to the through channel structure 2 and the base structure 3 is connected to the bottom of the through channel structures 2 for filtering leukocytes 5, erythrocytes 6 and hematoblasts 7 of blood cells 4, and serums 8. Referring to FIG. 10, the filtering channel structures 1 and the through channel structure 2 are assembled with each other in a array and arranged in the same plane.

Figure 11:
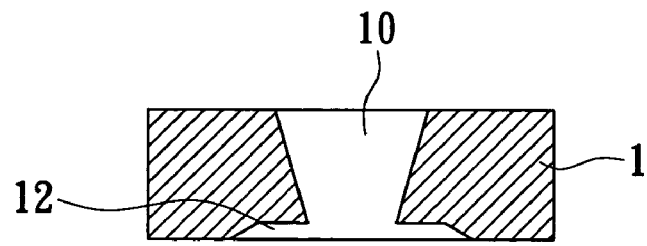
FIG. 11 a schematic cross-sectional view of the filtering channel structure made by MEMS technology of the present invention.

Referring to FIG. 11, the filtering channel structures 1 are made by MEMS technology and the steps of manufacturing each the filtering channel structure 1 include:
(1) preparing the silicon wafer;
(2) depositing a thin film on the double-faced of the silicon wafer;
(3) performing lithography on both faces of the silicon wafer;
(4) etching one face of the silicon wafer;
(5) etching another face of the silicon wafer;
(6) Bulk micromachining to form the first channel portion 12 and the first through hole 10; and
(7) covering the filtering channel structure 1 with a hydrophilic coating.

Figure 12:
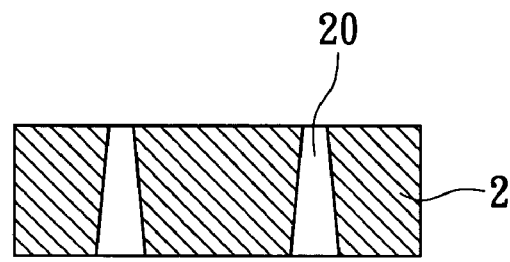
FIG. 12 a schematic cross-sectional view of the filtering channel structure made by MEMS technology of the present invention.

Referring to FIG. 12, the through channel structures 2 are made by MEMS technology and the steps of manufacturing each through channel structure 2 include:
(1) preparing the silicon wafer;
(2) depositing a thin film on one face of the silicon wafer;
(3) performing lithography on one face of the silicon wafer;
(4) etching one face of the silicon wafer to form the second through hole 20; and
(5) covering the through channel structure 1 with a hydrophilic coating.

Figure 13:
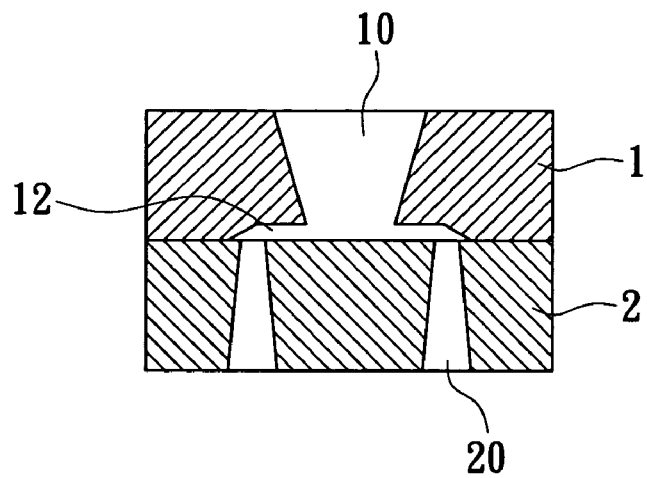
FIG. 13 a schematic cross-sectional view of the micro-filter made by MEMS technology of the present invention.

Referring to FIG. 13, one of the filtering channel structures 1 is connected to one of the through channel structure 2, so that a different channel width is defined between the first channel portion 12 and the second through hole 20 for filtering the blood cells.

To sum up, the micro-filter for filtering the blood cells of the present invention has two advantages, which include:
(1) the filtering channel structures 1 and the through channel structure 2 are connected to each other and made by MEMS technology to provide more than two filtering effects.
(2) the micro-filter is made by MEMS technology to reduce the dimensions and the cost of the micro-filter.

Those skilled in the art will readily observe that numerous modification and alterations of the device may be made while retaining the teachings of the invention. Accordingly, the above disclosure should be construed as limited only by the metes and bounds of the appended claims.

What is claimed is:

1. A micro-filter comprising:
   a plurality of filtering channel structures, each including a first through hole and two first channel portions opposite to each other on both sides of the first through hole, wherein each first channel portion consists of a plurality of first channels, each of the first channels includes a respective first opening, and the first channels are parallel to each other; and
   a plurality of through channel structures, each including two second through holes aligned with the first channel portions respectively and a second channel portion located between the two second through holes, wherein the second channel portion consists of a plurality of second channels parallel to each other, each of the second channels includes a respective second opening;
   wherein the plurality of the filtering channel structures and the through channel structures are stacked alternatingly and parallely over one another, and the width of the first and second openings of the consecutive channel structures are set to separate blood cells to leukocytes, erythrocytes, hematoblasts and serum, in that order.

2. The micro-filter as claimed in claim 1, wherein the filtering channel structures are respectively attached to the through channel structures by an anode joint.

3. The micro-filter as claimed in claim 1, wherein the filtering channel structures and the through channel structures are made of a silicon wafer.

4. The micro-filter as claimed in claim 1, comprising
   a base structure connected to a bottom of the through channel structures and having a plurality of through hole therein to strengthen the micro-filter.

5. The micro-filter as claimed in claim 1, wherein the plurality of filtering channel structures and the plurality of through channel structures are made of the same material.

* * * * *